(12) United States Patent
Wang et al.

(10) Patent No.: US 9,234,865 B2
(45) Date of Patent: *Jan. 12, 2016

(54) ANALYTE TEST INSTRUMENT HAVING IMPROVED VERSATILITY

(71) Applicant: Abbott Diabetes Care Inc., Alameda, CA (US)

(72) Inventors: Yi Wang, San Ramon, CA (US); Shridhara Alva Karinka, Pleasanton, CA (US); Gurdial Sanghera, Newton, MA (US)

(73) Assignee: Abbott Diabetes Care Inc., Alameda, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/575,753

(22) Filed: Dec. 18, 2014

(65) Prior Publication Data

US 2015/0168338 A1 Jun. 18, 2015

Related U.S. Application Data

(63) Continuation of application No. 12/623,894, filed on Nov. 23, 2009, now Pat. No. 8,916,036, which is a continuation of application No. 10/326,008, filed on Dec. 19, 2002, now abandoned.

(51) Int. Cl.
G01N 27/327 (2006.01)
G01N 33/487 (2006.01)

(52) U.S. Cl.
CPC ........ *G01N 27/3272* (2013.01); *G01N 27/3273* (2013.01); *G01N 33/48785* (2013.01); *G01N 33/48771* (2013.01)

(58) Field of Classification Search
CPC .................. G01N 27/3272; G01N 27/3273
See application file for complete search history.

(56) References Cited

U.S. PATENT DOCUMENTS

| | | | |
|---|---|---|---|
| 5,282,950 A | 2/1994 | Dietze et al. | |
| 5,366,609 A | 11/1994 | White et al. | |

(Continued)

FOREIGN PATENT DOCUMENTS

| | | |
|---|---|---|
| EP | 0651250 | 5/1995 |
| JP | 11042098 | 2/1999 |

(Continued)

OTHER PUBLICATIONS

JPO computer-generated English language translation of Yoshinobu Tokuno JP 2001-281197 A, patent published Oct. 10, 2001.
JPO machine-generated English language translation of Ikeda et al. JP 11-042098 A , downloaded Feb. 4, 2014.
Product description for Electrochemical Processor Model 1000 manufactured by Rank Brothers downloaded Feb. 4, 2014, which is believed current as of Feb. 2002.
Operating Manual for Electrochemical Processor Model 1000 and Model 2000 manufactured by Rank Brothers Issue Feb. 1, 2002.

*Primary Examiner* — Alexander Noguerola
(74) *Attorney, Agent, or Firm* — Edward J. Baba; Bozicevic, Field & Francis LLP

(57) ABSTRACT

An analyte test instrument that has a test strip circuitry that can be configured using information provided by a calibration strip to perform assays with test strips having two electrodes and test strips having three electrodes. The analyte test instrument of this invention comprises:
(a) a test port for receiving a test strip;
(b) a microprocessor for executing instructions downloaded into the analyte test instrument;
(c) a test strip circuit capable of having a plurality of configurations, the configurations being set by the microprocessor, whereby an assay can be performed using the test strip.

20 Claims, 9 Drawing Sheets

(56) References Cited

U.S. PATENT DOCUMENTS

| | | |
|---|---|---|
| 5,509,410 A | 4/1996 | Hill et al. |
| 5,582,697 A | 12/1996 | Ikeda et al. |
| 5,628,890 A | 5/1997 | Carter et al. |
| 5,873,990 A | 2/1999 | Wojciechowski et al. |
| 6,117,289 A | 9/2000 | Yamamoto et al. |
| 6,129,823 A | 10/2000 | Hughes et al. |
| 6,377,894 B1 | 4/2002 | Deweese et al. |
| 6,616,819 B1 | 9/2003 | Liamos et al. |
| 6,713,308 B1 | 3/2004 | Lu et al. |
| 6,773,564 B1 | 8/2004 | Yugawa et al. |
| 6,863,800 B2 | 3/2005 | Karinka et al. |
| 8,916,036 B2 * | 12/2014 | Wang et al. .............. 204/403.02 |
| 2003/0146110 A1 | 8/2003 | Karinka et al. |

FOREIGN PATENT DOCUMENTS

| | | |
|---|---|---|
| JP | 2001281197 | 10/2001 |
| JP | 2001311711 | 11/2001 |
| JP | 2002156358 | 5/2002 |
| WO | 9819159 | 5/1998 |
| WO | 9919507 | 4/1999 |
| WO | 0033072 | 6/2000 |

\* cited by examiner

ANALYTE TEST INSTRUMENT HAVING IMPROVED VERSATILITY

BACKGROUND OF THE INVENTION

1. Field of the Invention

This invention relates to analyte test instruments that perform electrochemical assays on biological samples. More particularly, the invention relates to analyte test instruments that can perform electrochemical assays by using different modes of operation.

2. Discussion of the Art

Electrochemical assays for determining the concentrations of analytes in samples comprising complex mixtures of liquids have been developed. Such electrochemical assays can be performed with test strips, i.e., biosensors in the form of strips. Test strips can function in an invasive manner (i.e., as probes that come into contact with a body fluid, such as whole blood or subcutaneous fluid). Test strips can function in a non-invasive manner (i.e., as strips that come into contact with blood withdrawn by a syringe or a lancing device). In particular, test strips for biomedical applications (e.g., whole blood analyses) have been developed for the determination of glucose levels in biological samples.

An analyte test instrument is an instrument can be used to perform electrochemical assays to determine the concentration of an analyte (e.g., glucose) in a biological sample (e.g., blood). To operate such an instrument, a user inserts a test strip into a test port in the instrument. The instrument displays a "ready" indication to the user and allows sufficient time for the user to deposit a biological sample on the test strip. When a sufficient quantity of the sample reaches the working electrode of the test strip, an electrochemical reaction occurs. The reaction produces an electrical response, such as a change in current. The electrical response is detectable by the analyte test instrument. The analyte test instrument converts the detected signal into data that corresponds to information relating to the analyte and displays the information to the user. The instrument may be able to store a series of such measurements and provide the stored information to the user via a display or to an external processor via a data link.

All commercially available electrochemical assays employing test strips for determining the concentration of glucose employ test strips having two electrodes. See, for example, WO 99/19507, incorporated herein by reference, which describes a test strip having two electrodes. In a test strip having two electrodes, the test strip has (1) a working electrode and (2) a dual-purpose reference/counter electrode. The reaction that takes place at the working electrode is the reaction that is required to be monitored and controlled. The second electrode is called a dual-purpose reference/counter electrode because this electrode acts as a reference electrode as well as a counter electrode. No current passes through an ideal reference electrode, and such an electrode maintains a steady potential; current does pass through a dual-purpose reference/counter electrode, and thus, the dual-purpose reference/counter electrode does not maintain a steady potential during the measurement. At low currents and/or at short durations of time for measurement, the shift in potential is small enough such that the response at the working electrode is not significantly affected, and hence the dual-purpose reference/counter electrode is designated a dual-purpose reference/counter electrode. The dual-purpose reference/counter electrode continues to carry out the function of a counter electrode; however, in this case, the potential that is applied between the dual-purpose reference/counter electrode and the working electrode cannot be altered to compensate for changes in potential at the working electrode.

Electrochemical assays employing test strips having three electrodes employ a test strip having (1) a working electrode, (2) a reference electrode, and (3) a counter electrode. See, for example, U.S. Ser. No. 10/062,313, filed Feb. 1, 2002, incorporated herein by reference. As in the test strip having two electrodes, the reaction that takes place at the working electrode is the reaction that is required to be monitored and controlled. The functions of the reference electrode and the counter electrode are to ensure that the working electrode actually experiences the conditions desired, i.e. the correct potential intended to be applied. The function of the reference electrode is to measure the potential at the interface of the working electrode and the sample as accurately as possible. In an ideal situation, no current passes through the reference electrode. The function of the counter electrode is to ensure that the correct potential difference between the reference electrode and the working electrode is being applied. The potential difference between the working electrode and the reference electrode is assumed to be the same as the desired potential at the working electrode. If the potential measured at the working electrode is not the potential desired at the working electrode, the potential that is applied between the counter electrode and the working electrode is altered accordingly, i.e., the potential is either increased or decreased. The reaction at the counter electrode, as measured by the current, is also equal and opposite to the charge transfer reaction, as measured by the current, occurring at the working electrode, i.e., if an oxidation reaction is occurring at the working electrode then a reduction reaction will take place at the counter electrode, thereby allowing the sample to remain electrically neutral.

An analyte test instrument designed for test strips having two electrodes could not be used if an assay employing a test strip having three electrodes needs to be performed. The user would have to use a separate analyte test instrument. If the user wanted to perform a set of assays that required strips having two electrodes and a set of assays that required strips having three electrodes, these assays could not be performed on the same analyte test instrument.

An analyte test instrument for electrochemical assays often requires the user to calibrate the instrument for each batch of test strips. U.S. Pat. No. 5,366,609, incorporated herein by reference, describes a calibration technique that requires a read-only-memory (ROM) key for operation and calibration of an analyte test instrument. A ROM key is inserted into a port (i.e., the ROM key port) that is distinct from the port for a test strip (i.e., the test port). A test strip is inserted into the test port after the ROM key is inserted into the ROM key port. The ROM key must remain in the ROM key port during both the calibration and the operation of the instrument. The ROM key contains specific data, including algorithms, for carrying out procedures for determining the concentration of an analyte in a biological sample applied to one of a batch of test strips associated with the ROM key. The data stored in the ROM key include measurement delay times, incubation times, the number of measurements to be taken during a measurement period, various thresholds against which voltage levels can be compared, values of excitation voltage levels applied to the strip during a test procedure, glucose value conversion factors, and a variety of failsafe test threshold values. In addition, the ROM key can contain some or all of the code for the microprocessor that controls the performing of the assay. A microprocessor in the analyte test instrument uses the algorithms, the conversion factors, and the code provided by the ROM key as needed.

U.S. Pat. No. 6,377,894, incorporated herein by reference, describes an instrument requiring a ROM key for operation and calibration of the instrument. The ROM key is inserted into the test port of the instrument and data is downloaded from the ROM key by the instrument and stored in the memory of the instrument. The ROM key contains data needed for carrying out procedures for determining the concentration of an analyte in a biological sample applied to a test strip. The ROM key is removed so that test strips can be inserted into the test port to perform assays. Different ROM keys can be inserted into the instrument to provide data for the testing of different analytes on the same instrument. The instrument can communicate with the ROM key to determine the analyte for which the ROM key contains information. Calibration information can be stored in different locations in the memory of the instrument for each analyte the instrument is capable of testing. When a test strip is inserted into the test port, the instrument has the ability to recognize which analyte is being tested. The microprocessor in the instrument then recalls the instructions for carrying out procedures for determining the concentration of that analyte, and the instrument then performs the appropriate test.

The aforementioned patents do not describe how the electrical circuitry of the instrument can be reconfigured so that analytical tests that require different circuit configurations can be performed on the same instrument. The aforementioned patents do not describe how stored information relating to the configuration of the electrical circuitry of the instrument can be modified when an assay for a specific analyte needs to be modified. The aforementioned patents do not describe how stored information can be used to reconfigure the electrical circuitry of the instrument while a test, strip is being used. Accordingly, it would be desirable to provide an analyte test instrument that addresses the foregoing deficiencies.

SUMMARY OF THE INVENTION

In one aspect, this invention provides an analyte test instrument that has test strip circuitry that can be placed into different configurations by means of information provided by a calibration strip to perform assays with test strips having two electrodes and test strips having three electrodes. In another aspect, this invention provides methods for using the analyte test instrument to perform assays with test strips having two electrodes and test strips having three electrodes. The analyte test instrument of this invention comprises:

(a) a test port for receiving a test strip;
(b) a microprocessor for executing instructions downloaded into the instrument; and
(c) a test strip circuit capable of having a plurality of configurations, the configurations being set by the microprocessor, whereby an assay can be performed using a test strip that has been inserted into the test port.

In preferred embodiments, the analyte test instrument further includes a memory for storing instructions and information required for the operation of the instrument. However, in other embodiments, the memory can be removably attached to the instrument, as described previously in U.S. Pat. No. 5,366,609.

In one embodiment, the invention provides an analyte test instrument that can perform assays on a variety of different analytes. In order to perform these assays, a calibration strip is inserted into the test port. After communication is established between the calibration strip and the analyte test instrument, information (i.e., data or programs or both) involving the method(s) for performing the assay(s) are downloaded from the calibration strip, and, if the analyte test instrument has a memory, preferably stored in the memory of the analyte test instrument. In the analyte test instrument having a memory, the information is stored in the analyte test instrument after the calibration strip is removed. The stored information specifies whether the method(s) of the assay(s) requires a test strip having two electrodes or test strip having three electrodes.

In the performance of an assay, a test strip is inserted into the test port, and the identity of the assay is indicated, preferably by means of a pattern of conductive material applied to a major surface of the test strip, preferably the major surface that does not support the electrodes. The analyte test instrument then determines from the downloaded information whether the assay calls for a test strip having two electrodes or for a test strip having three electrodes. The appropriate electrical switches in the test strip circuit of the analyte test instrument are then opened or closed to establish the configuration of the test strip circuit appropriate for the test strip utilized in the assay, that is, a test strip having two electrodes or a test strip having three electrodes. A sample to be analyzed, typically a biological sample, is then applied to the test strip, and a reaction that generates an electrical response occurs. The electrical response is detected and measured by the analyte test instrument, and the concentration of the analyte tested is determined by means of the downloaded calibration information. The analyte test instrument then displays the concentration of the analyte. Assays that call for a test strip having two electrodes and assays that call for a test strip having three electrodes can be performed on the same analyte test instrument.

In another embodiment, the analyte test instrument of this invention features the capability of changing the method for performing an assay to determine the concentration of a particular analyte. In order to change the method for performing the assay, a new calibration strip is inserted into the test port. The instructions for the performing the new method of the assay for the particular analyte are then downloaded to the analyte test instrument, and, if the analyte test instrument has a memory, preferably stored in the memory of the analyte test instrument. When the test strip is inserted into the test port, the identity of the assay is determined. The appropriate electrical switches in the test strip circuit of the analyte test instrument are then opened or closed to establish the appropriate circuit configuration for the test strip utilized in the assay, that is, a test strip having two electrodes or a test strip having three electrodes. The circuit configurations are based on the information from the calibration strip most recently downloaded to the analyte test instrument. The same analyte test instrument can be used to perform an assay even if the test method is changed one employing a test strip having two electrodes to one employing a test strip having three electrodes, and vice versa.

In another embodiment of this invention, the analyte test instrument can employ both a two-electrode mode and a three-electrode mode during the same assay. The expression "two-electrode mode" refers to the test strip circuitry employed for operating an analyte test instrument with a test strip having two electrodes. The expression "three-electrode mode" refers to the test strip circuitry employed for operating an analyte test instrument with a test strip having three electrodes. The information previously downloaded from the calibration strip, and, preferably, stored in the memory of the analyte test instrument, specifies what portion of the assay employs a test strip circuit configuration in a two-electrode mode and what portion of the assay employs a test strip circuit configuration in a three-electrode mode. A test strip is inserted into the test port, and the identity of the assay is indicated, preferably from a pattern of conductive material that has been applied to a major surface of the test strip, preferably the major surface that does not support the electrodes. The analyte test instrument then determines from the aforementioned downloaded information whether the assay requires a test strip circuit configuration in a two-electrode mode or a test strip circuit configuration in a three-electrode mode at the start of the assay. The appropriate electrical switches in the analyte test instrument are then opened or closed to establish the appropriate electrode mode. A sample to be analyzed, typically a biological sample, is then applied to the test strip, and a reaction that generates an electrical response occurs. During the performance of the assay, the appropriate electrical switches in the analyte test instrument are then opened or closed to establish the test strip circuit configuration for the appropriate electrode mode, which is a different electrode mode than was used at the start of the assay. The electrical response is detected and measured by the analyte test instrument, and the concentration of the analyte is determined by means of the downloaded calibration information. The analyte test instrument can then display the concentration of the analyte.

One example wherein the test strip circuit configuration is switched during an assay involves an assay in which it may be preferred to use a test strip having three electrodes for the advantages provided by the use of a test strip having three electrodes, such as, for example, improved control of voltage at the working electrode. However, it may be desired to exclude the working electrode of the test strip having three electrodes during the sample detection phase of the assay. In this case, the test strip circuit for the two-electrode mode is preferred during this sample detection phase of the assay. Accordingly, test strip circuit configurations for both the two-electrode mode and the three-electrode mode are desired within the course of an assay. It is assumed that an assay involves operational steps beginning with the insertion of the test strip into the analyte test instrument and obtaining the result of the assay.

The analyte test instrument of this invention makes it possible for the user to perform assays with test strips having two electrodes and test strips having three electrodes with the same instrument. The analyte test instrument of this invention makes it possible for an assay to be modified without having to discard the instrument. The analyte test instrument of this invention makes it possible for the mode of operation to change during the performance of an assay without intervention from the user.

DETAILED DESCRIPTION

Figure 1:
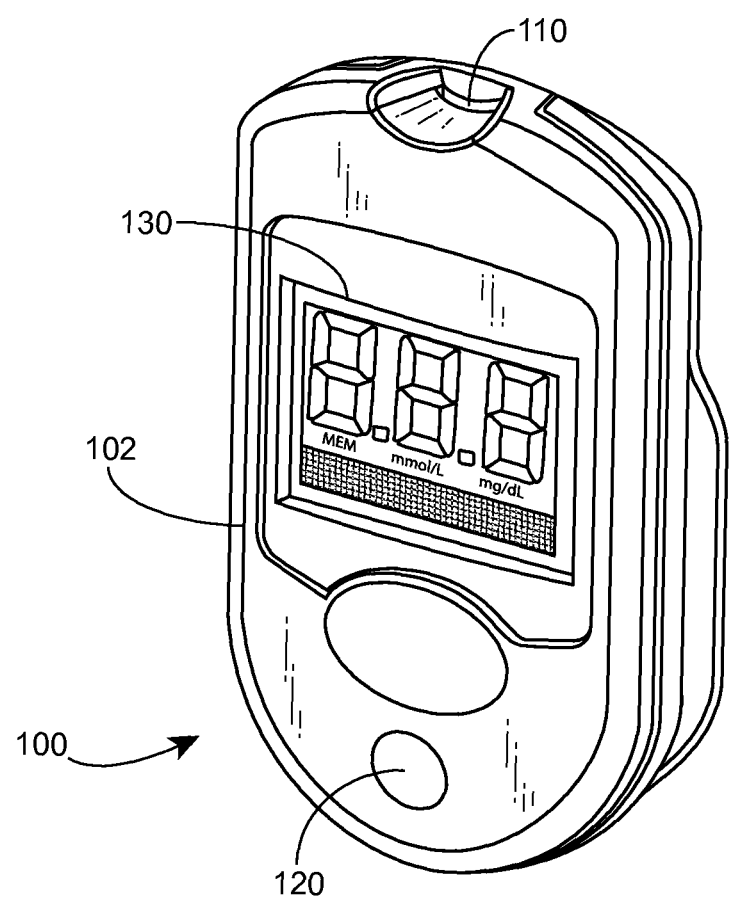
FIG. 1 is a perspective view of an embodiment of an analyte test instrument suitable for use in this invention.

As used herein, the expression "test strip having two electrodes" and other expressions relating to tests strips having two electrodes refer to test strips that have a working electrode and a dual-purpose reference/counter electrode. The expression "test strip having three electrodes" and other expressions relating to tests strips having three electrodes refer to test strips that have a working electrode, a counter electrode, and a reference electrode, the reference electrode being separate from the counter electrode. A "test strip having two electrodes" can have one or more additional electrodes, so long as the strip has a dual-purpose reference/counter electrode that performs the functions of both a reference electrode and a counter electrode. For example, a test strip having two electrodes can have a trigger electrode, which is an electrode that detects when a sufficient quantity of sample has been applied to the test strip. A "test strip having three electrodes" can have one or more additional electrodes, so long as the test strip has one electrode for performing the function of a reference electrode and another electrode for performing the function of a counter electrode. For example, a test strip having three electrodes can have a dummy electrode, which is an electrode that is similar to the working electrode, but lacks the substance that reacts with the analyte (see, for example, U.S. Pat. No. 5,628,890), or a trigger electrode dedicated to the sole function of detecting when a sufficient quantity of sample has been applied to the test strip (see, for example, U.S. Pat. No. 5,582,697).

As stated previously, all commercially available electrochemical test strips for determining the concentration of glucose employ two electrodes—(1) a working electrode and (2) a dual-purpose reference/counter electrode. As stated previously, electrochemical systems having three electrodes employ (1) a working electrode, (2) a reference electrode, and (3) a counter electrode.

Electrochemical systems employing test strips having three electrodes have the requirement that little or no current pass between the working electrode and the reference electrode. This requirement is achieved by using high impedance operational amplifiers in the electrical circuits of these systems. High impedance operational amplifiers are expensive; consequently, electrochemical systems that perform assays with test strips having three electrodes are expensive. These expensive systems are generally used only in research and are not practical from a cost standpoint for use by diabetics for glucose monitoring at home.

A test strip having three electrodes would be preferred in any electrochemical measurement that involves the application of an external voltage and measurement of current. However, due to constraints of sample volume (lower volume requirements), all electrochemical test strips commercially available use only two electrodes. Precise control of the voltage difference between the working electrode and the reference electrode must be maintained, but such control is difficult to achieve in a test strip having two electrodes. In known analyte test instruments, the electrical components of an analyte test instrument designed for test strips employing two electrodes would not operate with test strips employing three electrodes.

Referring now to FIG. 1, an analyte test instrument 100 comprises a housing 102, which contains the electrical and electronic components of the analyte test instrument. The analyte test instrument 100 comprises a test port 110, a push button 120, and a display 130. The test port 110 is a multi-purpose test port, which comprises a slot into which a user inserts test strips and calibration strips. The test port 110 comprises a slot assembly capable of receiving a strip, such as a test strip or a calibration strip. The test port 110 can have a plurality of electrical contacts capable of electrically engaging such a strip when the strip is inserted into the test port 110. The push button 120 allows the user to control the analyte test instrument 100. In particular, the push button 120 is used to turn the instrument on and off, to recall information stored in the instrument, to respond to messages displayed, and to set some of the configuration control parameters for the instrument. The push button 120 can also provide access to menus generated by software contained in the analyte test instrument 100. The display 130 is a device that gives information in a visual form. The display 130 is typically a screen. The information given typically includes, but is not limited to, test results, messages to the user, information stored in the memory of the analyte test instrument.

In one embodiment, one or more replaceable batteries (not shown) installed via a battery compartment at the rear of the analyte test instrument 100 (not shown) provide power for the analyte test instrument 100. It should be understood, however, that any source of power capable of providing a suitable direct (DC) voltage can provide power to the analyte test instrument 100.

Figure 2:
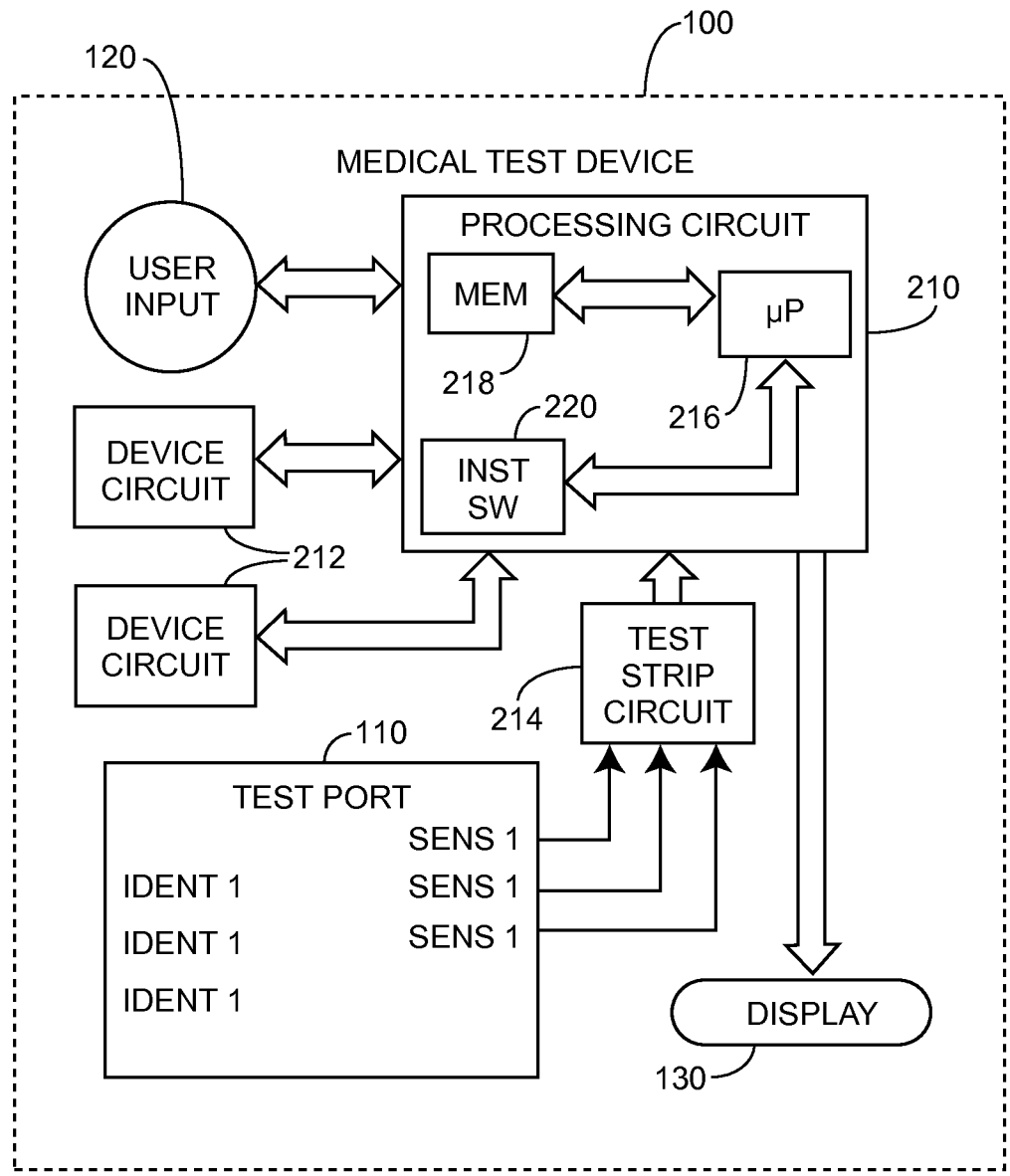
FIG. 2 is a block diagram that illustrates electronic components of an analyte test instrument suitable for use in this invention.

FIG. 2 is a block diagram that shows the interrelationship among the electronic components of an analyte test instrument 100. In addition to the aforementioned test port 110, push button 120, and display 130, all of which are accessible from the exterior of the analyte test instrument 100, the analyte test instrument 100 comprises a processing circuit 210, at least one device circuit 212, at least one test strip circuit 214, a microprocessor 216, and a memory 218.

The purpose of the processing circuit 210 is to enable a strip that is engaged in the test port 110 to communicate with the microprocessor 216 and the memory 218. For example, the processing circuit 210 can send signals to the test port 110 to determine the identity of the strip inserted therein, i.e., to determine whether the strip is a calibration strip or a test strip.

The device circuit(s) 212 and the test strip circuit(s) 214 can comprise analog, digital, or mixed-signal circuits, application-specific integrated circuits (ASICS), and passive and active electrical components. The device circuit(s) 212 can perform various electrical functions required by the analyte test instrument 100, such as driving the display function 130 and the clock functions for a microprocessor 216. In other words, the device circuit(s) carries instructions from the microprocessor 216 to various functional components of the analyte test instrument 100 so that these components can perform their intended functions. Test strip circuit(s) 214 can perform analog-to-digital (A/D) conversion of signals received at the test port 110 from a test strip and can perform digital-to-analog (D/A) conversion of signals received from the microprocessor 216. In other words, the test strip circuit(s) transmits information between the microprocessor 216 and the test strip. For example, the test strip circuit(s) is used to ensure that the proper voltage is being applied to the test strip and that the proper value of current generated at the test strip is being measured by the microprocessor 216.

The microprocessor 216 is an integrated circuit that contains the entire central processing unit of a computer. The memory 218 is a unit of a computer that preserves information for the purpose of retrieval. Such information may include, but is not limited to, measurement delay time(s), sample incubation time(s), number of measurements to be taken during an assay, threshold(s) against which voltage level(s) can be compared, value(s) of excitation voltage level(s) applied to a test strip during an assay, analyte value conversion factors, failsafe assay threshold value(s), and configurations of circuitry of the analyte test instrument.

In a preferred embodiment, the memory 218 comprises at least 1K of random access memory (RAM). In more preferred embodiments, the memory 218 has sufficient additional capacity to store a multiplicity of assay results.

Instrument software 220 is responsive to information received at the test port 110 from a calibration strip. The instrument software 220 uses the information received to control the operation of the analyte test instrument 100. The instrument software 220 also controls operations of the analyte test instrument 100 that are independent of information introduced or generated at the test port 110. For example, the instrument software 220 can enable the user to recall assay results and assay information, can provide various warning, error, and prompting messages, can permit setting of date and time, can control transmission of data to external devices, can monitor power level or battery level or both, and can provide indications to the user if power drops below a specified level.

Figure 4A:
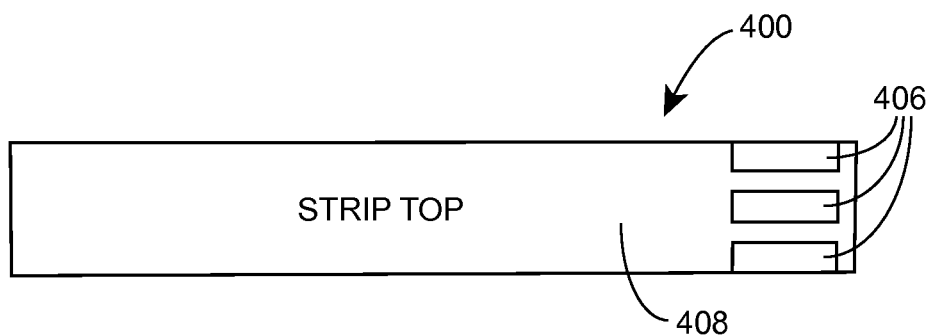
FIG. 4A illustrates a top plan view of test strip that is suitable for use with the analyte test instrument of this invention.
Figure 4B:
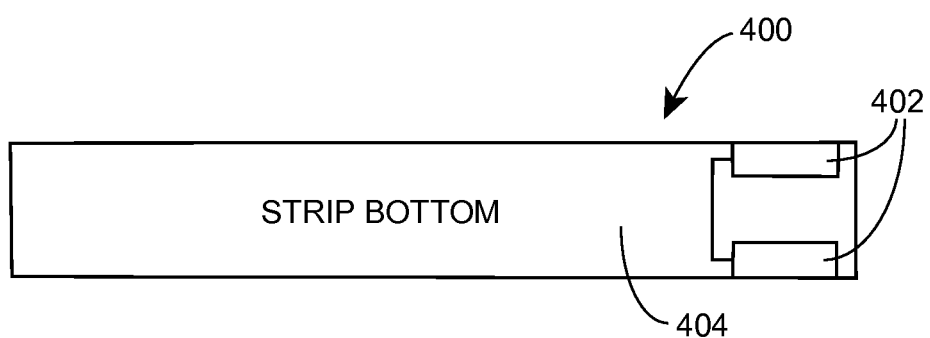
FIG. 4B illustrates a bottom plan view of test strip that is suitable for use with the analyte test instrument of this invention.

In the embodiment illustrated in FIG. 2, the test port 110 includes six electrical contacts, which are labeled IDENT1, IDENT2, IDENT3, SENS1, SENS2, and SENS3. When a strip is inserted into the test port 110, the major surfaces of the strip engage the electrical contacts of the test port 110, thereby enabling the analyte test instrument 110 to identify a pattern of conductive material on the top major surface of the strip, on the bottom major surface of the strip, or on both major surfaces of the strip. In a preferred embodiment, the pattern of conductive material on an inserted strip that interacts with the electrical contacts IDENT1, IDENT2, and IDENT3 indicates whether the inserted strip is a calibration strip or a test strip. This embodiment is shown in FIGS. 4A and 4B, which will be described later. If the inserted strip is a test strip, the type of analyte to be determined by the assay to be performed with the test strip is also identified (e.g., glucose, ketone bodies, etc.). The engagement of the electrical contacts and the strip identification process are described in more detail in U.S. Pat. No. 6,377,894, incorporated herein by reference. The electrical contacts labeled SENS1, SENS2, and SENS3 relate to the electrodes that are involved in performing analytical tests.

Figure 3A:
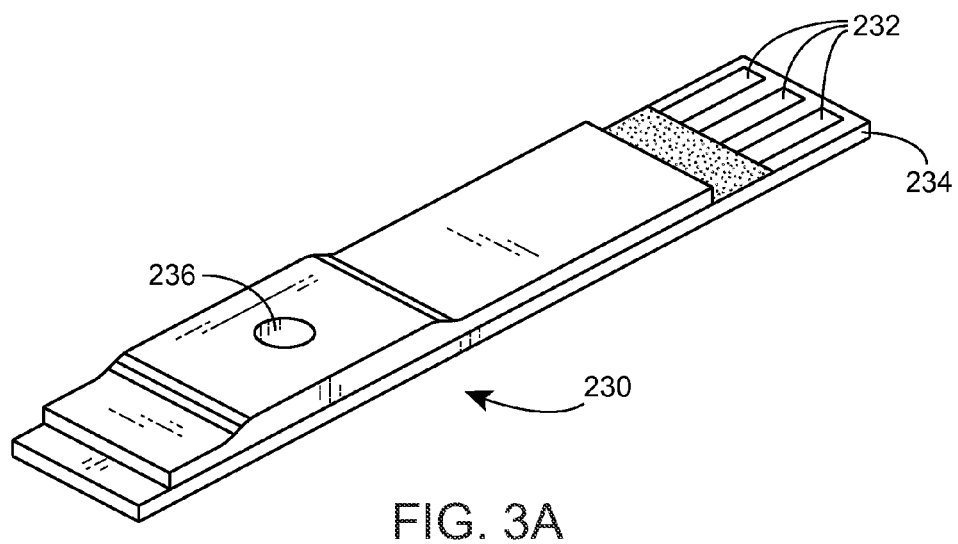
FIG. 3A is a perspective view of a test strip that is suitable for use with the analyte test instrument of this invention.

FIG. 3A illustrates in more detail a test strip 230. A plurality of electrical contacts 232 is provided at the end 234 of the test strip 230 that is inserted into the test port 110. Upon insertion of the test strip 230 into the test port 110, the electrical contacts 232 contact the electrical contacts SENS1, SENS2, and SENS3. Typically, a sample, e.g., a drop of blood, undergoing the assay is placed for testing on the reaction area 236 of the test strip 230. The reaction area 236 is the area where the sample contacts the electrodes of the test strip 230 (i.e., the working electrode and the dual purpose reference/counter electrode in the strip having two electrodes and the working electrode, the reference electrode, and the counter electrode in the strip having three electrodes). When a sufficient quantity of sample is deposited on the reaction area 236, an electrochemical reaction occurs, whereby a flow of electrons produces an electrical response, such as a change in current. The response is detectable by the analyte test instrument 100. The analyte test instrument 100 converts the detected response into data that is correlated with information relating to the analyte and displays the information to the user.

Figure 3B:
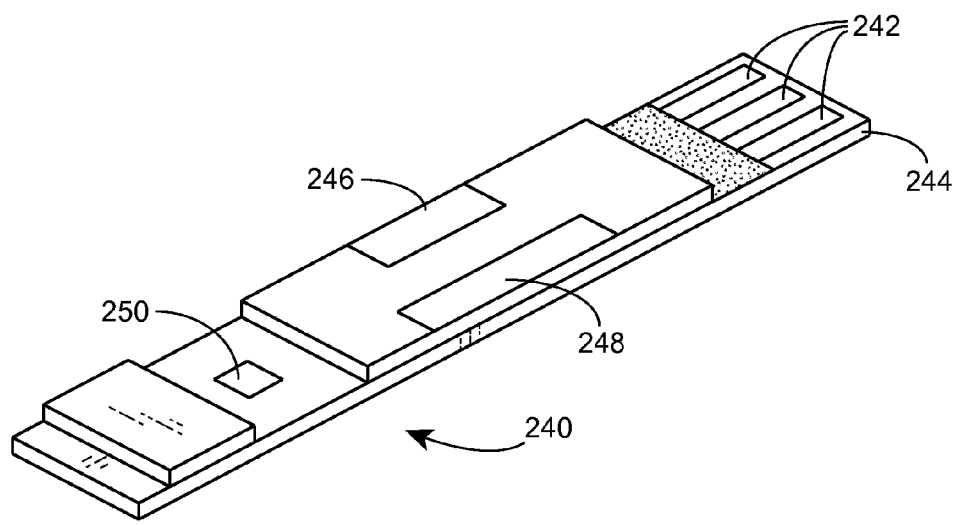
FIG. 3B is a perspective view of a calibration strip that is suitable for use with the analyte test instrument of this invention.

FIG. 3B illustrates a ROM-type calibration strip 240. In one embodiment, a ROM-type calibration strip 240 is associated with a package (not shown) of test strips 230. A plurality of electrical contacts 242 is provided at the end 244 of the calibration strip 240 that is inserted into the test port 110. In one embodiment, the calibration code 246 and manufacturing lot number 248 are printed on the calibration strip 240 and are visible to the user. In another embodiment, the lot number is stored in a read-only-memory (ROM) 250 in binary coded decimal (BCD) format.

The ROM 250, which is in electrical communication with the electrical contacts 242, encodes information relating to algorithm(s) for processing data obtained in an assay with a test strip. The ROM 250 can also encode information relating to the calibration code 246 and manufacturing lot number 248 as well as other parameters, as described in U.S. Pat. No. 6,377,894, incorporated herein by reference. The assays are not performed with the calibration strip 240. Rather, the calibration strip 240 delivers the information, the algorithms, the parameters, and the procedures that are required to characterize an assay to the analyte test instrument 100. The ROM 250 is capable of storing and downloading to the analyte test instrument 100 parameters that characterize an assay as having a two-electrode format or a three-electrode format.

Referring to FIGS. 4A and 4B, a test strip 400 has a pattern of conductive material 402 on the major surface 404 thereof that does not support the electrodes 406. The electrodes 406 are supported on the major surface 408 of the test strip 400. Different patterns of conductive material 402 can be used to specify different assays (e.g., glucose, ketone bodies, etc.). For each different assay, the pattern of conductive material 402 is disposed in such a way that the electrical contacts IDENT1, IDENT2, and IDENT3 of the test port 110 interact with the conductive material in the pattern to identify the type of assay that will be performed by the test strip 400, such as, for example, glucose, ketone bodies, lactate. A device circuit 212, such as an ASIC (see FIG. 2), identifies the type of assay that will be performed by the test strip 400 by determining the pattern of connection of the conductive material 402 on the major surface 404 of the test strip 400.

When a strip (e.g., calibration strip, glucose test strip, ketone bodies test strip, etc.) is inserted into test port 110 of the analyte test instrument 100, the analyte test instrument 100 detects the presence of the strip and performs a procedure to determine whether the strip is a calibration strip or a test strip for determination of the concentration of an analyte. First, the instrument software 220 polls the test port 110 to identify the function of the strip that has been inserted, i.e. calibration strip, test strip for determination of the concentration of an analyte. In one embodiment, the instrument software 220 attempts to communicate with the inserted strip by means of a protocol capable of operating with a serial EE-squared interface, such as that defined by the Dallas ROM protocol of Dallas Semiconductor, Dallas Tex. Such an interface provides single-wire communication. If the attempt to communicate is successful, the instrument software 220 proceeds to the ROM calibration procedure. If the attempt to communicate is unsuccessful, the instrument software 220 puts the analyte test instrument 100 into a brief wait mode (a predetermined time period), e.g., three to five minutes. If the analyte test instrument 100 fails to receive a signal indicating that a sample has been received during the waiting period, the analyte test instrument 100 shuts itself off automatically.

The receipt of a signal by microprocessor 216 indicates that the user is performing an assay for determination of the concentration of an analyte. Referring to FIG. 3A, when a test strip 230 is inserted into the test port 110, the electrical contacts 232 communicate with the analyte test instrument 100. When a sample (not shown) is added to the reaction area 236, the sample reacts with the reagents in the reaction area 236, thereby causing a flow of electrons to produce an electrical response, such as a change in current. The response is detectable by the analyte test instrument 100. The analyte test instrument 100 converts the detected signal into data corresponding to information relating to the analyte and displays the information to the user.

Figure 5:
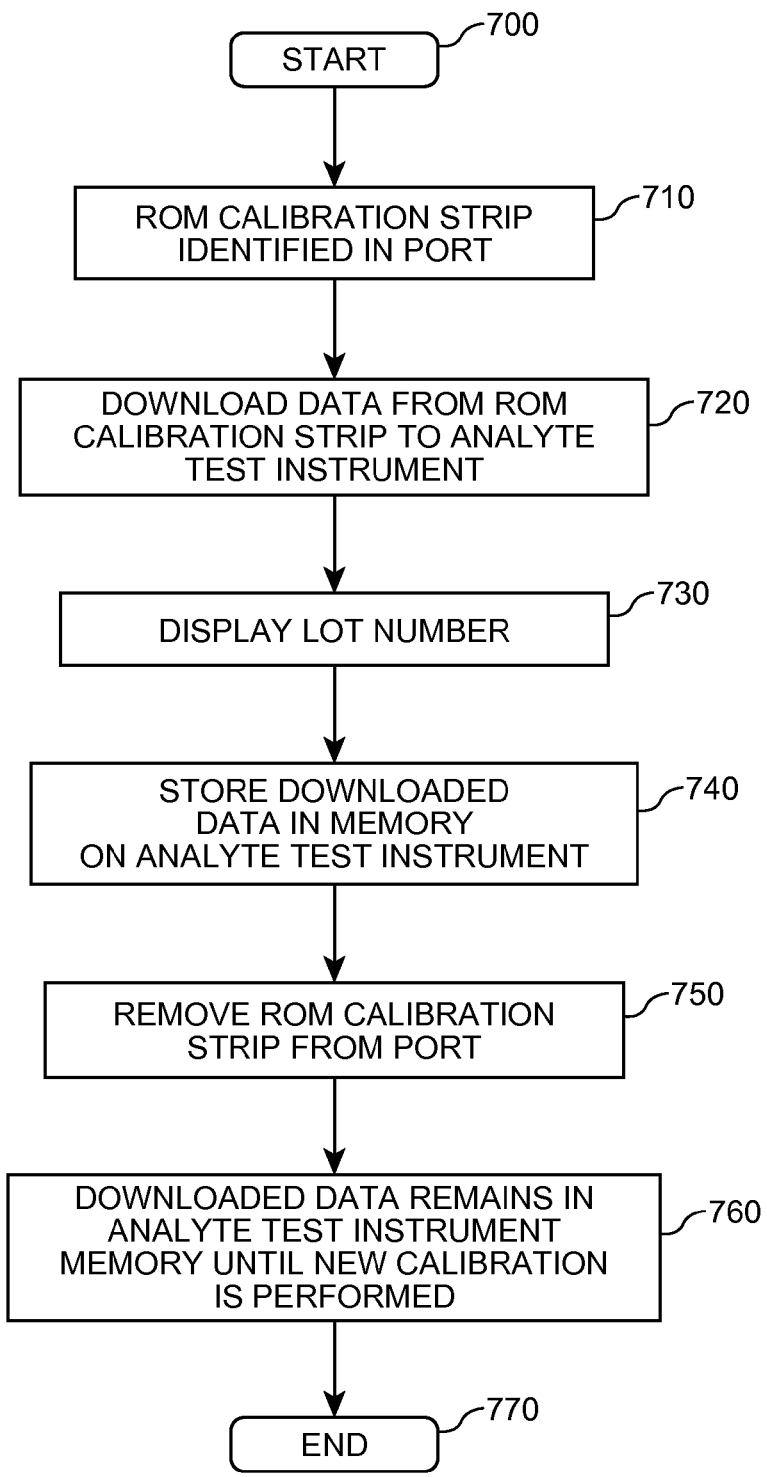
FIG. 5 is a flow chart illustrating a method for calibrating the analyte test instrument of this invention.

FIG. 5 illustrates the ROM calibration procedure when a calibration strip is introduced into the test port 110. When the instrument software 220 identifies the calibration strip 240 (step 710), data from the ROM 250 is downloaded to the analyte test instrument 100 (step 720). After the data from the ROM 250 has been downloaded to the analyte test instrument 100, the display 130 displays the lot number downloaded from the calibration strip 240 (step 730), as an indication that the calibration is complete. This data is stored in the memory 218 (step 740). The user can then remove the calibration strip from the test port 110 (step 750). The downloaded data remains in the memory 218 for use by the analyte test instrument 110 until a new calibration procedure is performed (step 760). In some embodiments, the analyte test instrument 100 can store more than one set of calibration data in the memory 218. For example, an analyte test instrument 100 capable of performing assays with a plurality of test strips 230 (e.g., glucose, ketone bodies), can store a set of calibration data for each type of test strip 230.

As described in U.S. Pat. No. 6,377,894, incorporated herein by reference, the downloaded and stored data comprises parameters, algorithms, operational procedures, and the like for controlling the operation of the analyte test instrument 100. In a preferred embodiment of this invention, the data comprise information that instructs the analyte test instrument to perform an assay with a test strip having two electrodes or with a test strip having three electrodes. In another preferred embodiment, the data comprise information that instructs the analyte test instrument 100 to begin an assay in a mode where the circuitry anticipates a test strip having two electrodes and then switch to a mode where the circuitry is changed to accommodate a test strip having three electrodes.

Operation

Figure 6:
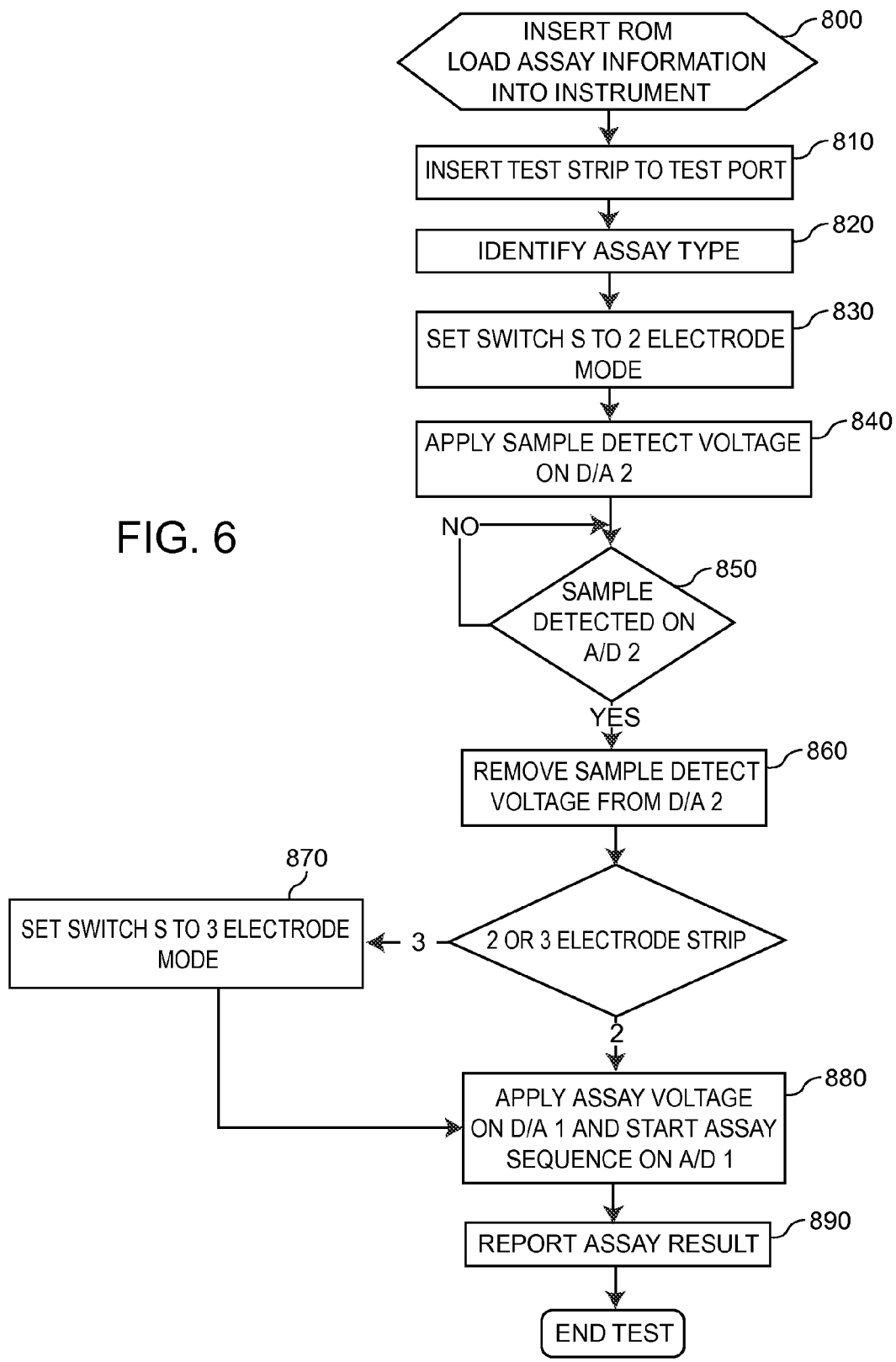
FIG. 6 is a flow chart illustrating a method for calibrating the analyte test instrument of this invention.

FIG. 6 depicts a flow chart of a method of performing an assay with the analyte test instrument of this invention. A calibration strip 240 is inserted into the test port 110 and information about types of assays (e.g., glucose, ketone bodies) and the configuration of the test strip circuit 214 (i.e., two electrodes or three electrodes) are downloaded and stored in the memory 218 of the analyte test instrument 100 (step 800). The calibration strip 240 is removed from the test port 110. A test strip 230 is inserted into the test port 110 (step 810). The microprocessor 216 of the analyte test instrument 100 determines whether the strip inserted into the test port 110 is a test strip 230 or a calibration strip 240 by transmitting a digital signal along a wire to the strip. If no signal is received from the strip, the microprocessor 216 has determined that the strip is a test strip 230. The microprocessor 216 then determines the pattern of electrical contacts on the major surface of the test strip 230 that does not support the electrodes (step 820). The aforementioned pattern of electrical contacts provides a signal to the microprocessor 216 indicating the assay that can be performed with the test strip 230 that has been inserted into the test port 110, such as, for example, a glucose assay, a ketone bodies assay. The microprocessor 216 then sets the switches of the test strip circuit 214 to the mode for a test strip having two electrodes (step 830). A sample is then introduced to the reaction area 236 of the test strip 230. A voltage is applied, and after a brief period of time, a small current can be detected (step 840). The current indicates that a sample, which covers the electrodes, has been detected (step 850). When the current is detected, the microprocessor 216 instructs a switch (not shown) in the device circuit 212 to open, thereby disconnecting the electrodes on the test strip from the test strip circuit 214 for a specified period of time (step 860), which period has been preset by the microprocessor 216. After the specified period of time, the switch (not shown) in the device circuit 212 is closed and the test strip circuit 214 remains in the two-electrode mode if the test strip is one having two electrodes, or the switches (not shown) in the test strip circuit 214 are set for a test strip having three electrodes (step 870) if the test strip is one having three electrodes. The appropriate electrode mode is determined by the microprocessor 216. The appropriate level of voltage is applied, and the current resulting from the electrochemical reaction between the sample and the reagents on the test strip is measured (step 880). The microprocessor 216 then converts the current measured into the appropriate value of concentration of analyte by means of parameters and algorithms that had been previously supplied by the calibration strip 240 and stored in the memory 218. The microprocessor 216 then instructs the display 130 to show the value of the concentration of analyte (step 890). Assays for different types of analytes and assays employing different types of test strips, i.e., test strips having two electrodes and test strips having three electrodes, can be carried out on the same analyte test instrument 100. If the characteristics of test strip for a particular assay are changed, such as, for example, a new assay for glucose is developed, the instructions for the analyte test instrument can be changed merely by using a new calibration strip; the analyte test instrument need not be discarded.

Figure 7A:
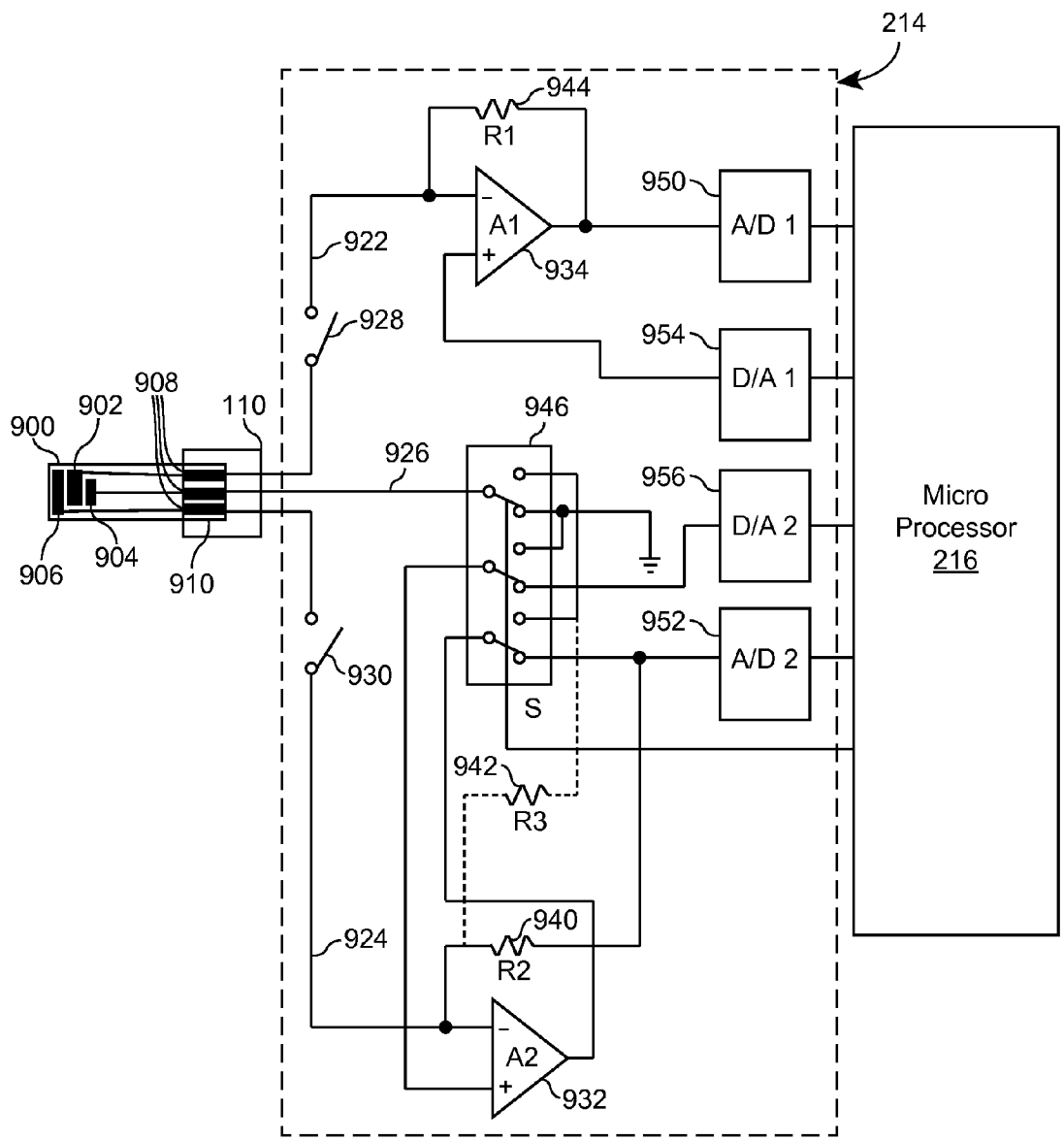
FIGS. 7A, 7B, and 8 are schematic diagrams that illustrates a test strip circuit that can be used to perform assays with two different types of test strips.
Figure 7B:
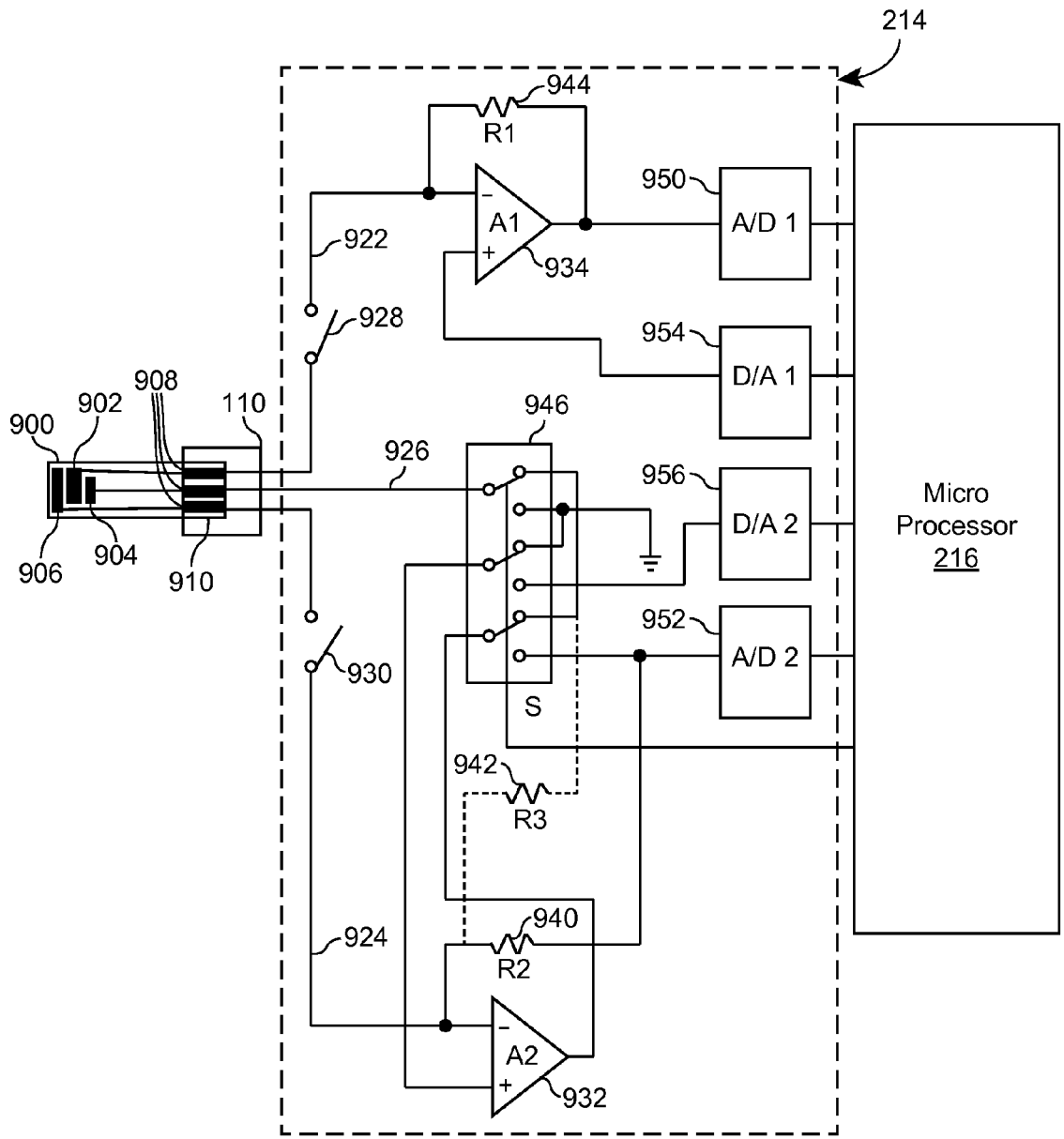
Figure 8:
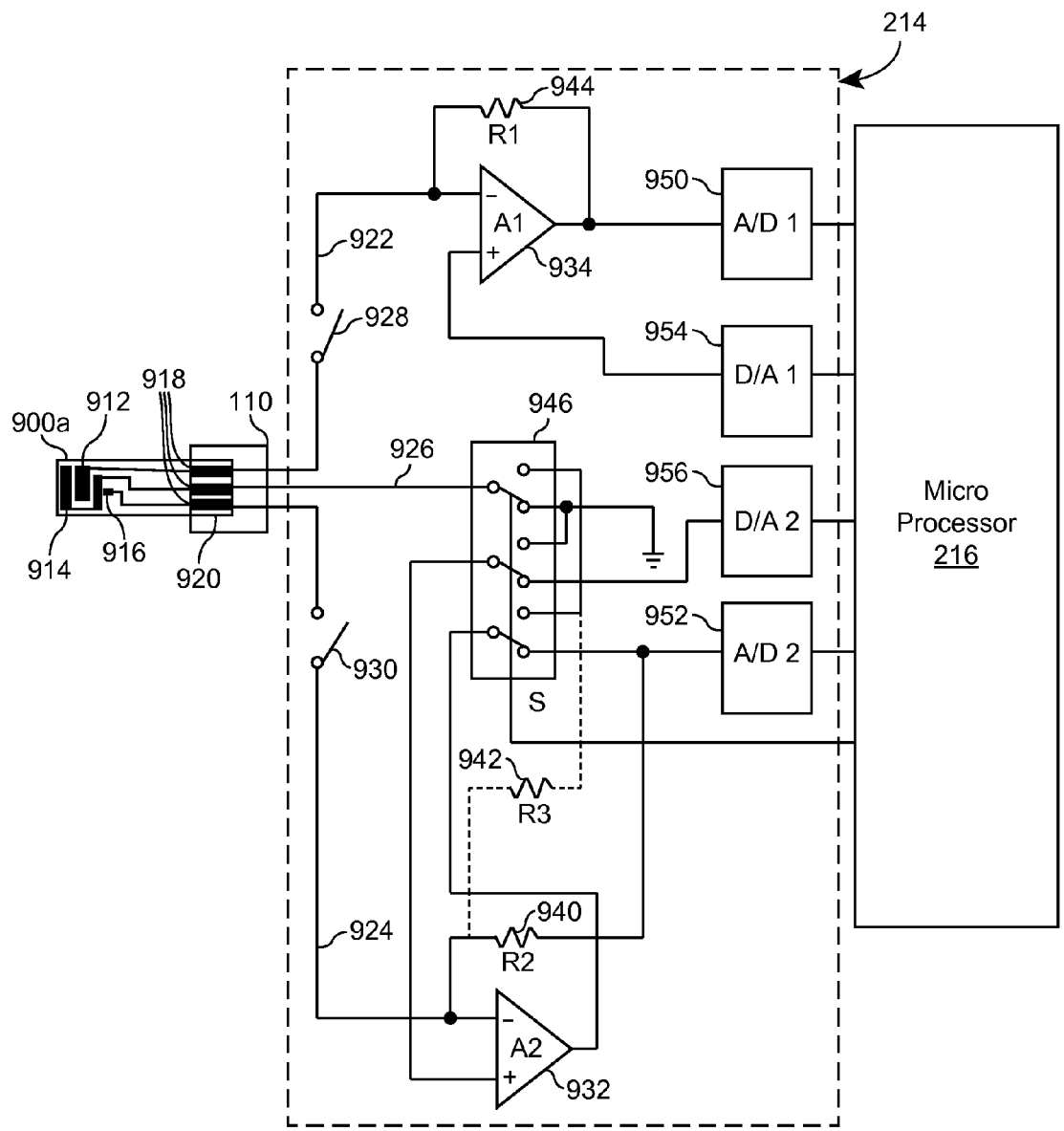

FIG. 7A, FIG. 7B, and FIG. 8 illustrate a test strip circuit 214 that can be used to perform assays with two different types of test strips—a test strip having two electrodes and a test strip having three electrodes. FIG. 7A and FIG. 7B show a top view of a test strip 900 having three electrodes, the test strip inserted in the test port 110. The test strip 900 is shown without its insulating coating, whereby a working electrode 902, a counter electrode 904, and a reference electrode 906 are visible. The electrical contacts 908 at the end 910 of the test strip 900 are also visible. FIG. 8 shows a top view of a test strip 900a having two electrodes, the test strip inserted in the test port 110. The test strip 900a is shown without its insulating coating, whereby a working electrode 912, a dual-purpose reference/counter electrode 914, and a trigger electrode 916 are visible. The electrical contacts 918 at the end 920 of the test strip 900a are also visible. FIG. 3A shows a test strip 230 having an insulating coating 238 present. In FIG. 7A, the electrical contacts 908 at the end 910 of the test strip 900 are shown inserted into the test port 110, where they make contact with electrical contacts SENS1, SENS2, and SENS3. These electrical contacts are depicted in FIG. 2. The electrical contacts SENS1, SENS2, SENS3 make electrical contact with the active electrical components of the test strip circuit 214 through wires 922, 924, and 926, respectively. The wires 922 and 924 have switches 928 and 930, respectively, controlled by the microprocessor 216, located between the electrical contacts (not shown) of the test port 110 and the test strip circuit 214. The switches 928 and 930 are used to connect or disconnect the electrical contacts SENS1 and SENS3 from the test strip circuit 214. FIG. 7A also shows operational amplifiers 932 and 934; resistors 940, 942, and 944; microprocessor-controlled switch 946; two analog-to-digital (ND) converters 950 and 952; and two digital-to-analog (D/A) converters 954 and 956. The microprocessor 216 shown in FIG. 7A is part of the processing circuit 210. The processing circuit is shown schematically in FIG. 2.

The test strip circuit 214 is first set in the two-electrode mode by the microprocessor 216. FIG. 7A shows switch 946 set in the two-electrode mode. The working electrode 902 is disconnected from the test strip circuit 214 by means of a microprocessor-controlled switch 928 in the wire 922. The D/A converter 956 receives a digital voltage instruction from the microprocessor 216 and applies an analog voltage, 400 mV, between the counter electrode 904 and the reference electrode 906 by means of the operational amplifier 932. The microprocessor 216 continues to interrogate the A/D converter 952. When a sufficient quantity of the sample is applied to the test strip 900 to result in a fluid connection between the counter electrode 904 and the reference electrode 906, a current begins to flow between the two electrodes. When the current reaches a threshold, e.g., 0.5 microamperes, the microprocessor 216 opens the switch 930 in the wire 924 leading to the reference electrode 906 for a short period of time, e.g., from about 0 to about 10 seconds. The next instructions from the microprocessor 216 differ, depending on whether the assay employs a test strip having two electrodes or a test strip having three electrodes.

If the assay involves a test strip employing three electrodes, the switch 946 is set at shown in FIG. 7B. The microprocessor-controlled switches 928 and 930 in the wires 922 and 924, respectively, are closed. The D/A converter 954 receives a digital voltage instruction from the microprocessor 216 and applies an analog voltage, 200 mV, to the working electrode 902 by means of the operational amplifier 934. The current originating at the working electrode 902 as a result of the reaction of the sample with the reagent is converted by the A/D converter 950 to a digital signal that is received by the microprocessor 216. The microprocessor 216 receives the digital signal from the A/D converter 950 at a specific time or at specific times. The microprocessor 216 can receive data from the A/D converter 950 at more than one time window, and the data from the different time windows can be used to perform error checks on the assay. Typical time windows for the microprocessor 216 to receive data are 4 to 5 seconds and 8 to 10 seconds. The microprocessor 216 uses the digital signal to calculate a concentration of analyte in the sample by using calibration factors supplied by a calibration strip. The concentration can then be displayed on the display 130 of the analyte test instrument 100.

If the assay employs a test strip having two electrodes, the switch 946 remains in the position shown in FIG. 8. The test strip circuit 214 is first set in the two-electrode mode by the microprocessor 216. FIG. 8 shows the switch 946 set in the two-electrode mode. The working electrode 912 is disconnected from the test strip circuit 214 by means of the microprocessor-controlled switch 928 in the wire 922. The D/A converter 956 receives a digital voltage instruction from the microprocessor 216 and applies an analog voltage, 400 mV, between the trigger electrode 916 and the dual-purpose reference/counter electrode 914 by means of the operational amplifier 932. The microprocessor 216 continually interrogates the D/A converter 952. When a sufficient quantity of sample is applied to the test strip 900a to result in a fluid connection between the fill trigger electrode 916 and the dual-purpose reference/counter electrode 914, a current begins to flow between the two electrodes. When the current reaches a threshold, e.g., 0.5 microamperes, the microprocessor 216 opens the switch 930 in the wire 924 leading to the trigger electrode 916 for a short period of time, e.g., from about 0 to about 10 seconds. Because the assay employs a test strip having two electrodes, the switch 946 remains in the position shown in FIG. 8. The microprocessor-controlled switch 928 in the wire 922 is closed. The D/A converter 954 receives a digital voltage instruction from the microprocessor 216 and applies an analog voltage, 200 mV, to the working electrode 912 by means of the operational amplifier 934. The current originating from the working electrode 912 resulting from the reaction of the sample with the reagent is converted by the A/D converter 950 into a digital signal that is received by the microprocessor 216. The microprocessor 216 receives the digital signal from the A/D converter 950 at a specific time or at specific times. The microprocessor 216 can receive data from the A/D converter 950 at more than one time window, and the data from the different time windows can be used to perform error checks on the assay. Typical time windows for the microprocessor 216 to receive data are 4 to 5 seconds and 8 to 10 seconds. The microprocessor 216 uses the digital signal to calculate a concentration of analyte in the sample by using calibration factors supplied by a calibration strip. The concentration can then be displayed on the display 130 of the analyte test instrument 100.

FIG. 7A, FIG. 7B, and FIG. 8 demonstrate that the same test strip circuit 214 can be used to analyze test strips having either two electrodes or three electrodes. The analyte test instrument of this invention is therefore more versatile than analyte test instruments of the prior art. The analyte test instrument of this invention can identify the type of test strip inserted into the instrument (i.e., one having two electrodes or one having three electrodes), and, by using stored calibration information, can configure the analyte test instrument appropriately without relying on input from the user. The analyte test instrument of this invention is therefore easier for the user to switch from one circuit to another than are analyte test instruments of the prior art.

The test strip circuit of the analyte test instrument of this invention and the method wherein a two-electrode mode is employed at the beginning of the assay to detect when the test strip is filled allows measurements to be made with much less expensive operational amplifiers, thereby reducing the cost of the analyte test instrument while providing performance characteristics of expensive analyte test instruments.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A method for performing an assay using an analyte test instrument, the analyte test instrument comprising:
    a test port for receiving a test strip;
    a microprocessor for executing instructions downloaded to the analyte test instrument; and
    a test strip circuit that switches between a two electrode configuration and a three electrode configuration following sample application to the test strip and before removal of the test strip, wherein switching between the configurations comprises the microprocessor setting the switches of the test strip circuit from an assay with a test strip having two electrodes to an assay with a test strip having three electrodes or the microprocessor setting the switches of the test strip circuit from an assay with a test strip having three electrodes to an assay with a test strip having two electrodes, wherein the test strip circuit is in a two electrode configuration during a first portion of an assay and a three electrode configuration during a second portion of the assay,
    wherein the method comprises:
        inserting a test strip into the test port of the analyte test instrument, wherein the test strip circuit of the analyte test instrument is in a two electrode configuration;
        after inserting the test strip, applying a sample to the test strip;
        running a first portion of an assay on the sample applied to the test strip;
        switching the test strip circuit of the analyte test instrument from the two electrode configuration to a three electrode configuration;
        running a second portion of the assay on the sample applied to the test strip; and
        after running the second portion of the assay, removing the test strip from the test port.

2. The method according to claim 1, wherein the test port is configured to receive a calibration strip, which calibration strip is removable from the test port to allow a test strip to be inserted into the test port, and wherein the method comprises calibrating the analyte test instrument using a calibration strip prior to inserting the test strip into the test port.

3. The method according to claim 1, wherein the analyte test instrument is configured to determine the concentration of an analyte in the sample, and wherein the assay is an analyte concentration determining assay.

4. The method according to claim 3, wherein the analyte is selected from the group consisting of: glucose, a ketone body, and lactate.

5. The method according to claim 4, wherein the analyte is glucose.

6. The method according to claim 3, wherein the analyte test instrument comprises a display, and wherein the method comprises displaying a determined analyte concentration on the display.

7. The method according to claim 6, wherein the method comprises displaying one or more messages to a user of the analyte test instrument.

8. The method according to claim 7, wherein the displaying comprises displaying a warning message to a user of the analyte test instrument.

9. The method according to claim 1, wherein the analyte test instrument comprises a memory for storing instructions and information.

10. The method according to claim 9, wherein the memory is configured to store results of one or more assays performed using the analyte test instrument.

11. The method according to claim 10, comprising enabling a user of the analyte test instrument to recall and display the results of the one or more assays.

12. The method according to claim 1, wherein the analyte test instrument comprises software configured to generate menus accessible by a user of the analyte test instrument, and wherein the method comprises providing the user access to the menus.

13. The method according to claim 1, wherein the analyte test instrument is configured to transmit data to one or more external devices, and wherein the method comprises transmitting data to one or more external devices.

14. A method of performing a glucose concentration determining assay using a glucose test instrument, the glucose test instrument comprising:

a test port for receiving a glucose test strip;

a microprocessor for executing instructions downloaded to the glucose test instrument; and a test strip circuit that switches between a two electrode configuration and a three electrode configuration following sample application to the test strip and before removal of the test strip, wherein switching between the configurations comprises the microprocessor setting the switches of the test strip circuit from an assay with a test strip having two electrodes to an assay with a test strip having three electrodes or the microprocessor setting the switches of the test strip circuit from an assay with a test strip having three electrodes to an assay with a test strip having two electrodes, wherein the test strip circuit is in a two electrode configuration during a first portion of an assay and a three electrode configuration during a second portion of the assay, wherein the method comprises:

inserting a glucose test strip into the test port of the glucose test instrument, wherein the test strip circuit of the glucose test instrument is in a two electrode configuration;

after inserting the glucose test strip, applying a sample to the test strip;

running a first portion of a glucose concentration determining assay on the sample applied to the test strip;

switching the test strip circuit of the glucose test instrument from the two electrode configuration to a three electrode configuration;

running a second portion of the glucose concentration determining assay on the sample applied to the test strip; and after running the second portion of the glucose concentration determining assay, removing the test strip from the test port.

15. The method according to claim 14, wherein the test port is configured to receive a calibration strip, which calibration strip is removable from the test port to allow a test strip to be inserted into the test port, and wherein the method comprises calibrating the glucose test instrument using a calibration strip prior to inserting the glucose test strip into the test port.

16. The method according to claim 14, wherein the glucose test instrument comprises a display, and wherein the method comprises displaying a determined glucose concentration on the display.

17. The method according to claim 16, wherein the method comprises displaying one or more messages to a user of the glucose test instrument.

18. The method according to claim 17, wherein the displaying comprises displaying a warning message to a user of the glucose test instrument.

19. The method according to claim 14, wherein the analyte test instrument comprises a memory configured to store results of one or more glucose concentration determining assays performed using the glucose test instrument, and wherein the method comprises enabling a user of the glucose test instrument to recall and display the results of the one or more glucose concentration determining assays.

20. The method according to claim 14, wherein the glucose test instrument is configured to transmit data to one or more external devices, wherein the method comprises transmitting data to one or more external devices.

* * * * *